United States Patent [19]

Jacob

[11] 4,031,569
[45] June 28, 1977

[54] NASAL SEPTUM PLUG

[76] Inventor: H. John Jacob, 8344 Hendrie, Huntington Woods, Mich. 48070

[22] Filed: Mar. 15, 1976

[21] Appl. No.: 666,577

[52] U.S. Cl. .................................... 3/1; 128/1 R; 128/334 R
[51] Int. Cl.² ..................... A61F 1/00; A61F 1/24
[58] Field of Search .............. 3/1; 128/1 R, 140 N, 128/325, 334 R, 334 C, 335, 342

[56] References Cited

UNITED STATES PATENTS

| | | | |
|---|---|---|---|
| 3,807,409 | 4/1974 | Paparella et al. ...................... | 3/1 X |
| 3,874,388 | 4/1975 | King et al. ..................... | 128/334 R |

OTHER PUBLICATIONS

"Prosthesis for the Temporary Closure of a Tracheostomy Stoma," by K. D. Rudd et al., The Journal of Prosthetic Dentistry, vol. 16, No. 6, Nov.–Dec. 1966, pp. 1159–1161.

Primary Examiner—Ronald L. Frinks
Attorney, Agent, or Firm—Basile, Weintraub and VanOphem

[57] ABSTRACT

A device for plugging a hole in a septum comprises a cylindrical member having a disc integrally formed therewith and disposed on each end of the cylindrical member. The device is formed from a flexible, non-toxic, non-irritating material.

5 Claims, 3 Drawing Figures

U.S. Patent
June 28, 1977
4,031,569
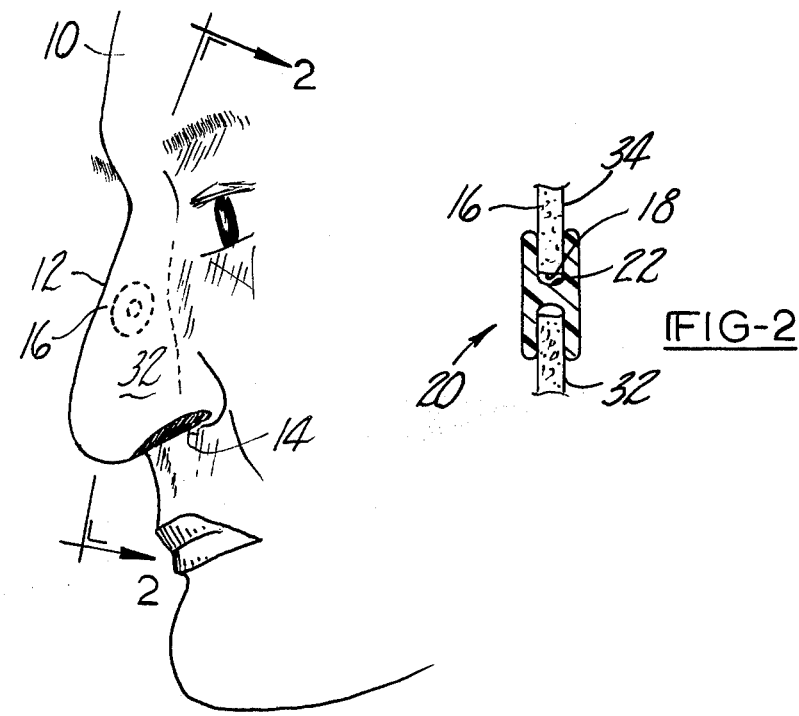
FIG-1
FIG-2
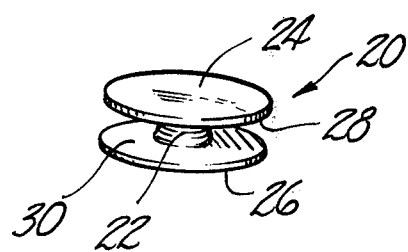
FIG-3

NASAL SEPTUM PLUG

BACKGROUND OF THE INVENTION

1. Field of the Invention

The present invention pertains to medical appliances. More particularly, the present invention pertains to nose-related medical appliances. Even more particularly, the present invention pertains to medical appliances which are insertable into body passages.

2. Prior Art

As is known to those skilled in the art to which the invention pertains there is a tendency for people who contact tuberculosis, as well as, silicosis to develop a hole or aperture in their septums. This is, also, true with respect to persons who undergo surgery to correct a deviated septum.

The hole developed in the septum, while not being medically dangerous, can lead to some respiration difficulties, as well as creating a pressure differential in the nasal passages by the flow of air through the hole.

It is estimated that there are approximately three million people in the United States who have such holes in their septums.

Heretofore, however, the prior art, to applicant's knowledge, has failed to direct its attention to this problem. The art has developed devices for facilitating breathing. See, inter alia, U.S. Pat. Nos. 2,323,199 and 3,145,711. Furthermore, the art has taught devices for insertion into body cavities; See, for example, U.S. Pat. No. 2,234,494, as well as other protective devices, as represented by U.S. Pat. No. 2,163,792. However, and as noted, the art has not, heretofore, directed its attention to the problem sought to be rectified hereby.

SUMMARY OF THE INVENTION

In accordance with the present invention there is provided a device for plugging a hole in a septum. The device hereof comprises a spool having a central cylindrical portion and a disc formed on each end of the cylinder. The discs are integrally formed with the central cylindrical portion.

In deploying the device hereof, the spool is inserted into the aperture or hole in the septum such that the central portion traverses the septum. The discs lie against the septum and seal off the aperture.

The plug hereof is formed from a non-toxic, chemically inert, non-irritating, flexible, synthetic material which can be formed into the present plug.

For a more complete understanding of the present invention reference is made to the following detailed description and accompanying drawing. In the drawing, like reference characters refer to like parts throughout the several views, in which:

BRIEF DESCRIPTION OF THE DRAWING

FIG. 1 is a side view of a person's head showing deployment of the device of the present invention;

FIG. 2 is a front elevational view of a septum having the present device associated therewith, and FIG. 3 is a perspective view of the device of the present invention.

DESCRIPTION OF THE PREFERRED EMBODIMENT

Now, and with reference to the drawing, there is depicted therein the head 10 of a person. For purposes of orientation of the deployment of the present invention, it is to be understood that the head includes a nose 12 having a pair of nasal passages 14 (only one of which is shown). The nasal passages 14 are separated by a medial cartilage 16, which is commonly known as the septum.

As hereinbefore noted, due to the contacting of certain diseases or as a result of certain surgical techniques, oftentimes an aperture or hole 18 may be developed through the septum 16.

In accordance with the present invention a device or septum plug, generally, denoted at 20, is utilized to plug up the hole 18.

The plug 20 comprises a central cylindrical or central portion 22. The cylindrical portion 22 has a length substantially equal to the diameter or width of the septum 16. The cylindrical portion 22 is adapted to be inserted through the aperture 18 and is sized and shaped for disposition within the aperture. Of course, depending on the configuration of the aperture 18, the precise configuration of the cylindrical portion 22 may vary. In any event, the portion 22 has a diameter equal to or slightly less than the diameter of the hole 18.

As clearly shown in FIGS. 2 and 3, a disc 24 and 26 is formed on each end of the cylindrical portion 22. The discs 24, 26 are intergrally formed with the cylindrical portion 22 at each end thereof. Generally, the discs 24, 26 have a diameter larger than the diameter of the cylindrical portion 22.

The plug 20 is constructed such that the opposed interior surfaces 28, 30 of the discs 24, 26, respectively, abut against the lateral sides 32, 34 of the septum.

The plug 20 hereof must be formed from a material which is medically acceptable. Accordingly, the plug 20 is formed from a non-toxic, non-irritating, chemically inert flexible material. Such materials are known an commercially available. They are sold under a plurality of trademarks such as SILASTIC and PROPLAST. Particularly preferred materials are the silicone rubbers, such as the dimethyl polysiloxane elastomers sold by DOW CORNING under the name SILASTIC. These compounds are documented in the art, such as, for example, as is found in U.S. Pat. Nos. 2,927,907; 3,035,016 and 2,833,742.

These compounds meet the criteria noted above and, in addition are highly flexible to facilitate their deployment in practicing the present invention.

In utilizing the present plug, it is inserted into one of the nasal passages. Thereafter, one of the discs is flexed through or otherwise inserted through the aperture 18 to cause the central portion 22 to extend through the aperture. Upon reaching the other nasal passage the disc conforms to its original shape with its interior surface abutting the associated lateral side of the septum about the periphery of the hole. Contemporaneously, the other disc has its interior surface abut against the other lateral side of the septum about the periphery of the hole, thereby sealing off the hole. This is done without any discomfiture to the user. The plug can be removed by reversing the procedure outlined above.

Having, thus, described the invention what is claimed is:

1. In a device for plugging a hole formed through a nasal septum, the improvement comprising:
   a. a central portion having opposed ends, the central portion being sized and shaped for disposition within the hole,
   b. a disc of greater diameter than the central portion formed on each end of the central portion, and wherein the device is a unitary, solid member which is formed from a chemically inert, non-toxic, non-irritating flexible material.

2. The improvement of claim 1 wherein:
a. the central portion has a diameter equal to or slightly less than the diameter of the hole, and
b. the discs have a diameter larger than the diameter of the hole, such that the discs are adapted to abut against the opposite lateral sides of the septum about the periphery of the hole.

3. The improvement of claim 1 wherein:
the device comprises a polysiloxane rubber.

4. The improvement of claim 3 wherein:
the polysiloxane rubber is a dimethyl polysiloxane elastomer.

5. In a method for plugging a hole formed through a nasal septum, the improvement comprising;
inserting through the hole the device of claim 1 such that the discs about against the opposite lateral sides of the septum about the periphery of the hole.

* * * * *